United States Patent
Leonhardt et al.

(10) Patent No.: US 6,372,241 B1
(45) Date of Patent: *Apr. 16, 2002

(54) PVC/TWINE DISPENSER FOR PHEROMONES

(75) Inventors: Barbara A. Leonhardt, Potomac; E. David DeVilbiss, Silver Spring, both of MD (US); Victor C. Mastro, Cotuit, MA (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 08/248,041

(22) Filed: May 24, 1994

Related U.S. Application Data

(63) Continuation of application No. 07/765,732, filed on Sep. 26, 1991, now Pat. No. 5,342,618.

(51) Int. Cl.$^7$ ............................................. A01N 25/10
(52) U.S. Cl. ..................... 424/411; 43/132.1; 424/405; 424/406; 424/413; 424/84; 523/122; 514/475
(58) Field of Search ................................. 424/405, 408, 424/409, 411, 412, 84, 406, 413, 78.31, 486; 523/122; 526/344; 43/132.1; 514/475

(56) References Cited

U.S. PATENT DOCUMENTS

| | | | |
|---|---|---|---|
| 601,183 A | * | 3/1898 | Thum ........................... 43/118 |
| 1,591,902 A | * | 7/1926 | Weinberg .................... 424/411 |
| 4,400,903 A | | 8/1983 | Seidenberger |
| 4,639,393 A | | 1/1987 | Von Kohorn et al. |

FOREIGN PATENT DOCUMENTS

| | | | | |
|---|---|---|---|---|
| AU | 25868 | * | 3/1930 | ................. 424/412 |
| GB | 2018593 | * | 10/1979 | ................. 424/408 |

* cited by examiner

Primary Examiner—Neil S. Levy
(74) Attorney, Agent, or Firm—M. Howard Silverstein; John D. Fado; Janelle S. Graeter

(57) ABSTRACT

A novel dispenser for the release of insect attractants has been invented for baiting insect traps. The dispenser is comprised of a flexible support coated with a polyvinylchloride (PVC)-insect attractant mixture. A PVC/twine dispenser has been found to be particularly effective for the release of the gypsy moth pheromone, (+)-disparlure.

10 Claims, 3 Drawing Sheets

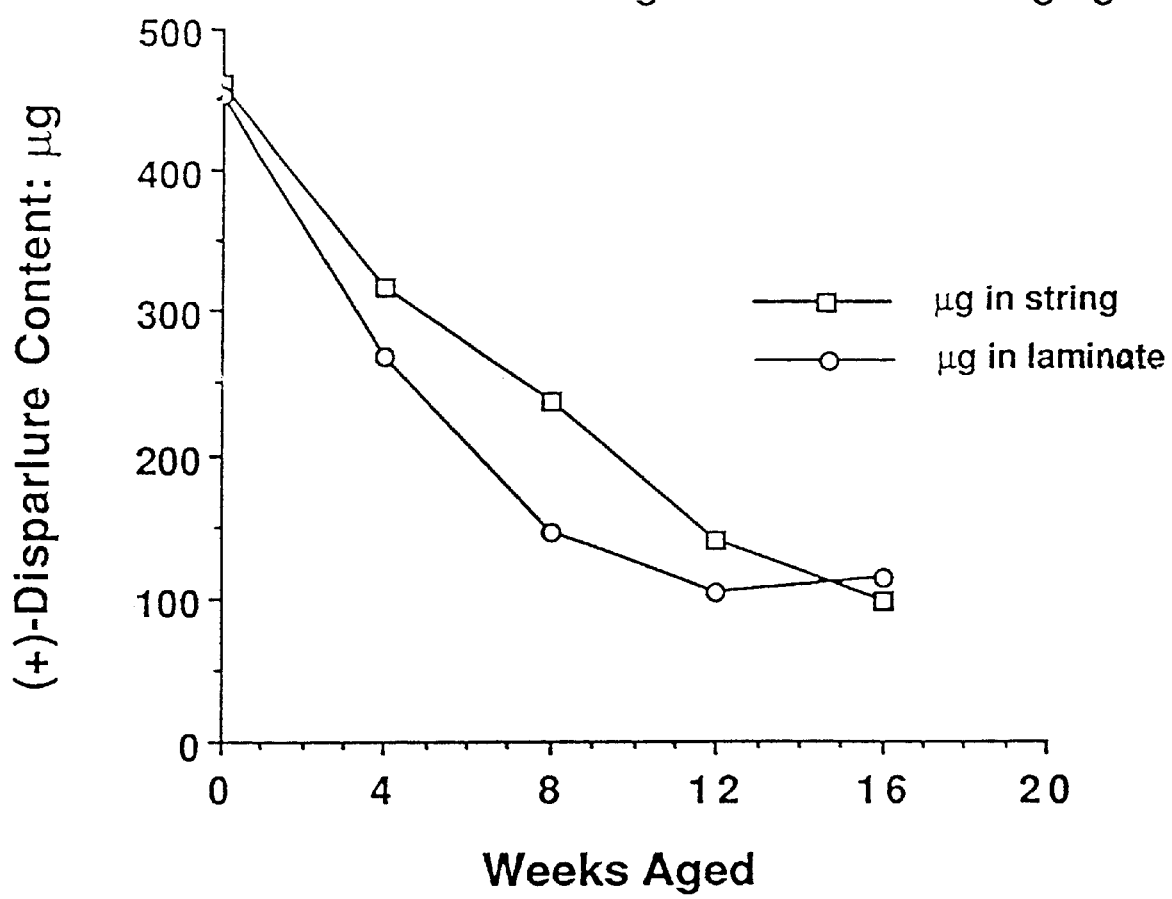

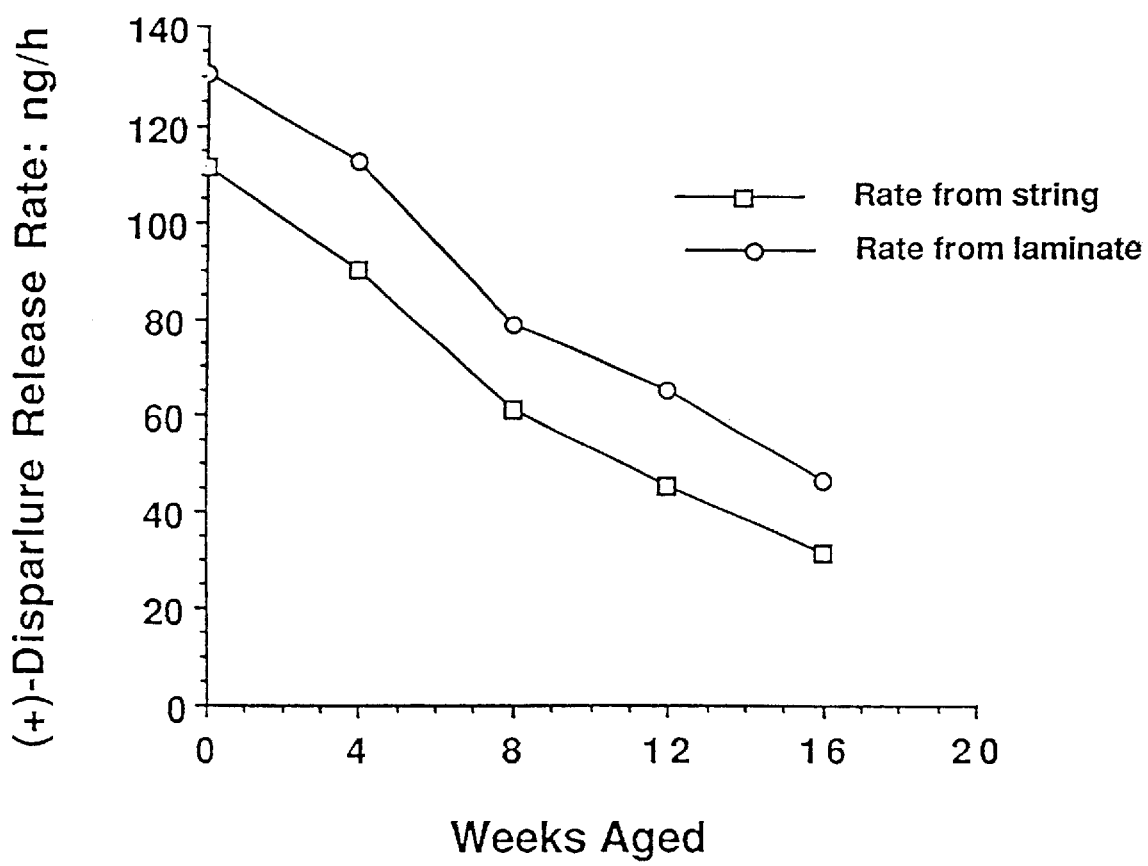

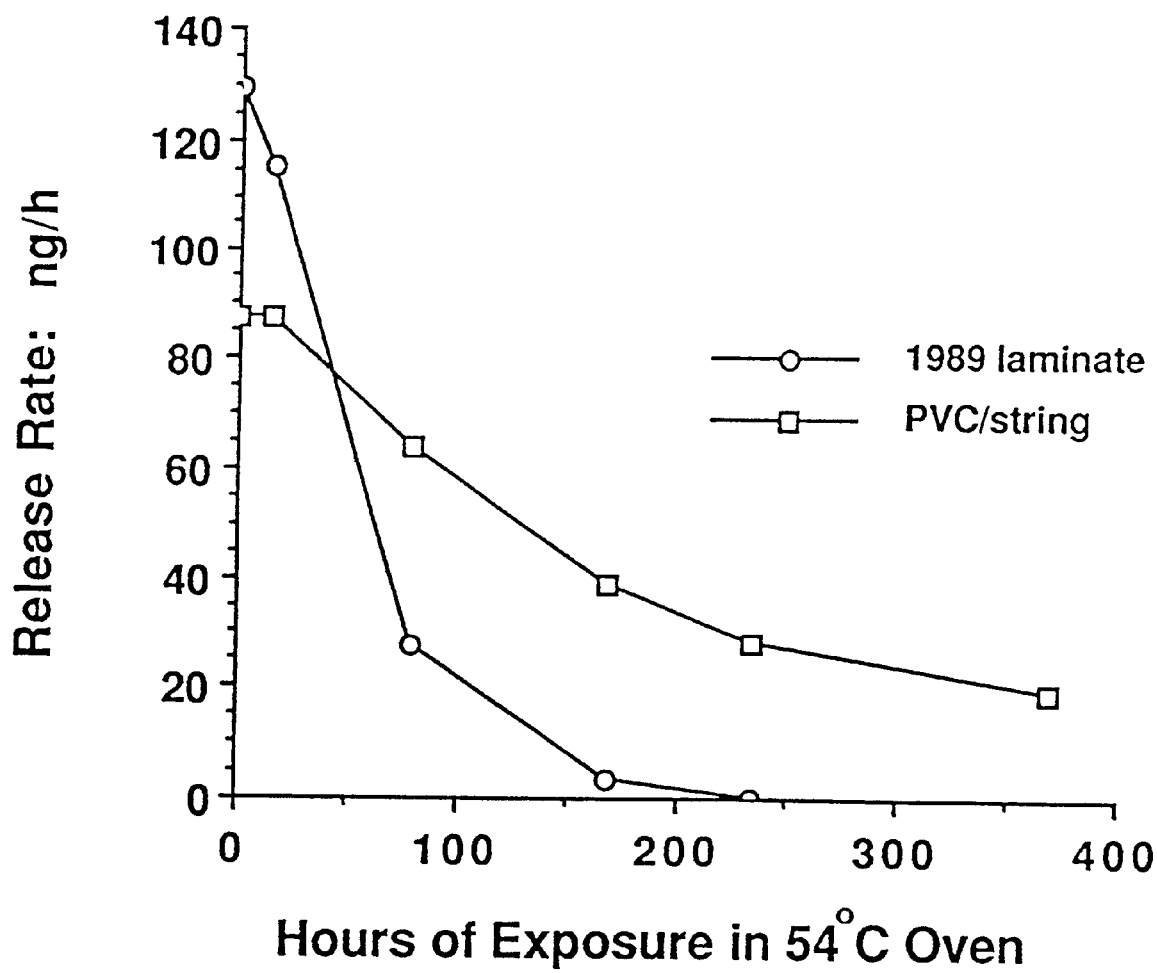
Figure 3: Comparison of (+)-Disparlure Release Rates from Oven-aged Dispensers

PVC/TWINE DISPENSER FOR PHEROMONES

This is a continuation of application Ser. No. 07/765,732 filed Sep. 26, 1991, now U.S. Pat. No. 5,342,618, herein incorporated by reference.

I. BACKGROUND OF THE INVENTION

The gypsy moth, Lymantria dispar L., is a major forest pest in the northeastern United States, and spot infestations appear elsewhere. Monitoring existing gypsy moth populations and detecting new populations is achieved by utilizing traps baited with polymeric, controlled-release dispensers containing the sex attractant pheromone, (7R,8S)-cis-7,8-epoxy-2-methyloctadecane, or (+)-disparlure, wherein male moths are lured into the traps by the pheromone. When such lures are used in conjunction with insecticides, the moths are killed inside the traps.

The pheromone, disparlure, was identified, synthesized and reported in the literature by Bierl et al. (*Science*, 170:87–89, 1970). The optical character of the pheromone structure was later determined to be the (+)-enantiomer by Yamada et al. (*J. Insect Physiol*, 22:755–761, 1976). The pheromone has since been used in traps for the detection of gypsy moth populations and is commercially available. Its relatively high cost, however, dictates that the dispenser utilized must deliver nearly all of its pheromone content over one entire flight season of the moth. Otherwise, residual pheromone in the dispenser at the end of the season is wasted when the dispenser is discarded. It is equally important that the supply of the pheromone not be depleted before the end of the flight season.

In these types of traps, therefore, one must regulate the amount of pheromone released from the dispenser in the trap so that there is a balance between a rate of release sufficient to lure the moth into the trap and the length of time that the trap must remain attractive (one flight period). The dispenser must not deliver the pheromone so rapidly that the trap does not provide adequate luring capabilities over the entire flight period of the moth.

The pheromone (+)-disparlure is sufficiently volatile that the compound must be formulated in a controlled-release dispenser in order to prolong its evaporation and thus extend the duration of its effectiveness. Since the early 1980's, a dose of approximately 500 mg of (+)-disparlure in a plastic laminate dispenser (Hercon Environmental Co., Emigsville, Pa.) has been used to bait a standard milk-carton gypsy moth trap used in all Federal and State detection programs (Schwalbe, C. P. in Technical Bull. 1584, USDA, Washington, D.C., pp. 542–549, 1981, Doane and McManus, ed.).

Normally, in assembling such traps, a twist tie is suspended within the trap by stapling it to the apex of the trap. The conventional pheromone dispenser is attached to the twist tie while an insecticide-impregnated strip is similarly attached near the dispenser. This is a labor intensive and tedious process since approximately 300,000 traps are required nationally each year.

Other commercial dispenser systems have been evaluated, but none has proven as effective as the plastic laminate device. Other commercial designs have included rubber septa, polyethylene tubes, silicone rubber, semi-permeable membranes over a reservoir and thermoset matrices.

A polyvinylchloride (PVC) pellet has also been tested which contains either 1250 or 2500 mg of (+)-disparlure. Even at these relatively high doses, the release rates are initially low, i.e. only 57 and 97 ng/hr, respectively, as compared to the release rate (ca. 130 ng/hr) given off by the standard laminate containing only 500 mg of pheromone. The low release rates per quantity of pheromone in the PVC pellets result from a low pheromone to polymer ratio and from a low surface area (ca. 75mm$^2$) for evaporation of the (+)-disparlure. After 16 weeks of greenhouse aging, which is equivalent to at least two flight seasons, these PVC pellets still contain at least 75% of their initial dose of pheromone. Thus, most of the pheromone is wasted in this type of dispenser since the planned use is for only one season.

PVC was used as a matrix for dispensing an insect pheromone by Fitzgerald et al. (*Environ. Entomol.*, 2:609–610, 1973) when high quantities (1–20% by weight) of the cabbage looper pheromone were incorporated in 70-mm long PVC cylinders. Since then, other pheromones were formulated in PVC forms, including the pheromone of the tobacco budworm, the boll weevil and the spruce budworm. The forms of the previously described PVC dispensers were a solid mass such as a slab, disc, rod, etc. which had a limited surface area for evaporation and release (See Weatherson, I. in *Insect Pheromones in Plant Protection*, Jutsum and Gordon, eds., John Wiley & Sons, New York, pp. 249–280, 1989, a review article).

The dose of pheromone per dispenser was substantially higher (2000–10,000 mg or more) in previously reported PVC applications than that used for the laminate dispenser (500 mg). Only PVC pellets designed for monitoring spruce budworm contained a relatively low dose (0.03% by weight), but those dispensers were shown to be unsatisfactory in field performance. The volatility of pheromones incorporated in previous PVC applications was higher and their cost substantially lower than that of (+)-disparlure, thus obviating a need to develop a PVC dispenser having an increased surface area for increasing its release rate or having an optimal efficiency for delivering its total pheromone content over a particular period of time. Thus, the need exists for a dispenser which will give a sufficient pheromone release rate while at the same time prolonging the rate of release such that pheromone is released over the entire insect flight period in a given area and delivers essentially all of the pheromone contained within the dispenser over that period.

II. SUMMARY OF THE INVENTION

We have now discovered that a dispenser which meets the above requirements can be made by coating a support with a mixture of an insect attractant and PVC, where the attractant is present in the mixture in an amount sufficient to lure an insect for which it is effective. Accordingly, it is an object of the invention to provide a novel dispenser which will provide a lure release rate sufficient to attract an insect for a time period which covers the entire flight season of the target insect. To meet this objective, a dispenser having a high surface area and coated with a thin film of the PVC-attractant mixture is provided, thereby permitting the dispenser to release attractant at an effectively high rate while at the same time prolonging its delivery over the entire flight season.

It is a further object of the invention to provide a trap comprising the novel dispenser in combination with a housing for the attachment of the dispenser. One embodiment of the trap optionally includes an insecticide in an amount sufficient to kill a trapped insect.

Another object of the invention is to provide a method of making the novel dispenser.

It is also an object of the invention to provide a method of using the novel dispenser for luring targeted insects of interest.

III. BRIEF DESCRIPTION OF THE DRAWINGS

FIG. 1 is a graph of aging data of (+)-disparlure as a function of the length of greenhouse aging.

FIG. 2 is a graph of (+)-disparlure release rates as a function of the length of greenhouse aging.

FIG. 3 is a graph of comparison data of (+)-disparlure release rates from oven-aged dispensers.

IV. DETAILED DESCRIPTION OF THE INVENTION

The primary novel feature of the instant invention is a flexible support that has been coated with a mixture of PVC and an insect attractant. A suitable flexible support includes any multi-stranded material such as twine, string, thread or cord that is weatherable for the duration of its use. Such supports may be cotton, nylon or the like, or blends of such materials, and they are usually twisted, braided or woven to give the material strength. The preferred support for this invention is a loose twisted twine, in particular nylon twine. Especially preferred is twisted nylon twine having a break strength of about 150 to 200 lbs., preferably about 165 lbs.

The flexible support is coated with a mixture of a curable PVC polymer and the insect attractant of interest. The particular PVC used can be obtained commercially and is not critical so long as it is conveniently curable by conventional methods either at room temperature or elevated temperatures, and with or without catalysts present. Suitable curable liquid PVCs may be obtained from Sinclair & Rush, St. Louis, Mo. and have the designation No. 516-89. Such PVCs are curable at elevated temperatures (up to about 200° C.) in an oven over short periods of time (about 1 minute to about 30 minutes).

Insect attractants are commercially available. They are blended with the curable PVC prior to coating the flexible support. The coating process glues the individual strands together to form one composite strand. After coating, the support should contain 10 to 100 mg/cm of the insect attractant, depending upon the volatility of the particular attractant used. The support can then be cut into pieces of a size to give the desired quantity of attractant. The high ratio of surface area per mg of PVC-insect attractant mixture in the dispenser enhances the rate of evaporation of the attractant and efficiently delivers most of the active compound over the duration of the flight period. Thus, the resulting product is a novel dispenser of a flexible material containing an insect attractant in a thin, cured PVC coating. As will be shown by the examples presented herein, this dispenser gives the optimum desirable release rate.

The novel dispenser of the instant invention contemplates the use of a broad range of insect attractants. A critical factor in the selection of a useful attractant is the volatility of the compound: the attractant must be sufficiently volatile when blended with PVC that it will maintain an effective release rate over a selected time period. Attractants of particular interest for use herein are pheromones of the cabbage looper, the tobacco budworm, the boll weevil, the spruce budworm and other insects for which a pheromone is known. Of particular interest is the use of the pheromone of the gypsy moth, (+)-disparlure.

The novel dispenser of the instant invention is prepared by initially coating the flexible support material with the PVC-attractant mixture by any conventional means such as dipping the support in the mixture or brushing the mixture onto the support. A particularly effective coating method involves threading the flexible material through a syringe barrel and out an orifice drilled in a Luer cap, leaving the remainder hanging out of the top of the barrel. Prepared PVC-attractant mixture is poured into the syringe barrel, and the support is pulled through the orifice. This procedure results in a thin, uniform coating on the support which gives the optimal release rate of the attractant. Following the coating procedure, the coated support is loosely coiled and laid on a glass plate in an oven to cure. The cured product is then cut into desired lengths for attachment to the particular trap configurations selected.

The novel trap of the instant invention may be effectively utilized in methods for monitoring known insect infestations or detecting new ones. Traps are placed in positions appropriate for the insect of interest for a period of time sufficient for the attractant to effectively lure insects into the trap. For example, when monitoring or detecting gypsy moth infestation, one deploys traps according to the instant invention, wherein the attractant is (+)-disparlure, in wooded areas suspected of having infestation over the entire flight period of the moth, usually from four to six weeks. For optimum results, the traps should be in place about one month before the flight period begins.

The novel invention is applicable in any instances wherein the insect attractant has sufficient volatility to provide an effective release rate. The experimentation required to determine such volatility would be considered of a routine nature and well within the level of skill in the art.

The following examples are intended only to further illustrate the invention and are not intended to limit the scope of the invention as defined by the claims.

The trap of the instant invention comprises the novel dispenser described supra and any conventional commercial trap which normally utilizes a dispenser suspended from, or attached to, the interior of the top of the trap. A milk carton type trap wherein the dispenser is fastened to the top interior apex of the carton is an example of such a trap. As discussed supra, conventional traps for the gypsy moth are made by fastening a twist tie to the interior apex of the trap, followed by attaching a dispenser to the twist tie, resulting in a two-step manufacturing method. An ancillary advantage of the novel dispenser is that it may be stapled directly to the apex of a trap thus eliminating the step of fastening a twist tie or other such attachment device to the trap. Optionally, an insecticide effective for the insect of interest may be additionally contained within the trap in a configuration which is suitable for acting on the particular target insect.

V. EXAMPLES

Laboratory and field tests have been designed to measure the efficacy of pheromone dispensers for gypsy moth detection. The measured parameters include: initial dose of pheromone, rate at which the pheromone is released, number of male moths captured per trap, and effect of duration of exposure on these quantities. The quantity of (+)-disparlure in a dispenser, either initially or after exposure, is measured by gas chromatography on a solvent extract of the dispenser using a known solution of (+)-disparlure as an external standard. The rate of release of (+)-disparlure from the dispenser is determined by trapping volatilized pheromone over a 6-hr period from a dispenser housed in a glass chamber within an oven set at 35° C. A constant air flow of 100 ml/min through the chamber transports the pheromone to the trap, and the quantity of trapped pheromone is then determined chromatographically.

Example I

Method of Making Dispensers

Liquid PVC, No. 516-89, was purchased from Sinclair & Rush, St. Louis, Mo. 63111. Twisted nylon twine, break strength 165 lb, no. 18, item no. 00089 was purchased from Duraline Products, Crowe Rope Co., Warren, Me. 04864. Neat (+)-disparlure, density=0.87 g/ml, was supplied and approved by USDA-APHIS.

The appropriate volume of (+)-disparlure was syringed into and blended with a known weight of the liquid PVC to give a concentration of 6.9 ml of attractant per gram of liquid PVC (or 0.6% by weight). Blending was carried out using a VirTis, homogenizer (VirTis Co., Inc., Gardiner, N.Y., model 45 or alternate) run at about ⅓ maximum speed for 1 minute. The end of a length (ca. 100 cm) of twine was threaded through a 5-ml glass syringe barrel with a Luer lok, fitting and out the orifice of a female Luer cap through which a 1.37 mm hole had been drilled. The end of the twine was coated with glue and shaped to a point to facilitate its insertion through the orifice. The PVC-(+)-disparlure mixture was poured into the syringe barrel, and the twine was pulled through the Luer cap orifice at a rate of approximately 30 cm/min. Additional mixture was added to the barrel as needed. The coated twine was loosely coiled and laid on a glass plate in a 170° C. oven for 3–5 min to cure. The resulting (+)-disparlure concentration in the coated twine was approximately 30 mg/cm. Lengths of 16.7 cm containing ca. 500 mg of attractant were cut for affixing to traps.

Example II

Greenhouse Aging

Since the gypsy moth flight is of relatively short duration, the effect of exposure on the dispensers and their measurable parameters was assessed by placing dispensers in a greenhouse set at 32–38° C. for periods of time ranging from 2 to 16 weeks prior to gypsy moth flight. These pre-aged dispensers were then compared with unaged dispensers in laboratory and field tests. The effect of greenhouse exposure on pheromone content and release rate and on moth capture can thus be determined and is shown in Table 1. Since greenhouse temperatures are higher than those generally found in field situations, dispenser aging is accelerated in the greenhouse. A dispenser which can remain attractive after 16 weeks in a greenhouse has been shown to remain highly attractive throughout a flight period. In the case of the conventional laminate dispenser, for example, a residual content of at least 100 mg of (+)-disparlure and a release rate of 30 ng/hr assures high insect capture. FIGS. 1 and 2 graphically show comparative data between conventional laminate dispensers and the novel PVC/twine dispenser of the instant invention with respect to pheromone content and release rate as a function of greenhouse aging. It can thus be seen that the novel dispenser compares favorably with the conventional dispenser in these two respects.

TABLE 1

Residual (+)-disparlure contents and release rates of laminate and PVC/twine dispensers after 0, 4, 8, 12, and 16 weeks of greenhouse aging.

| Dispenser | Content ($\mu$g) at Week | | | | | Release rate (ng/h) at Week | | | | |
|---|---|---|---|---|---|---|---|---|---|---|
| | 0 | 4 | 8 | 12 | 16 | 0 | 4 | 8 | 12 | 16 |
| laminate-1988 | 452 | 268 | 145 | 104 | 114 | 130.5 | 112.6 | 78.7 | 65.0 | 47.1 |
| laminate-1989 | 520 | 167 | 111 | 86 | 23 | 131.5 | 99.0 | 43.3 | 29.0 | 24.6 |
| PVC/twine | 461 | 316 | 237 | 139 | 97 | 111.5 | 89.8 | 61.2 | 45.9 | 31.6 |

Example III

Field Tests

Field tests were conducted to compare the PVC/twine dispenser with two lots of conventional laminate dispensers (1988 and 1989 lots). Greenhouse aging periods for each dispenser were 0, 4, 8, 12 and 16 weeks. Five replicates of each treatment were tested. Effectiveness was determined by numbers of male moths captured (n), which, for analytical purposes was transformed to $(n+0.5)^{1/2}$. Results are shown in Tables 1 and 2.

TABLE 2

Mean numbers of males[1] captured per trap in each of three observations in Test 1, 7/18–7/23, 1989.

| Dispenser | Weeks of Greenhouse Aging | | | | |
|---|---|---|---|---|---|
| | 0 | 4 | 8 | 12 | 16 |
| laminate-1988 | 87.8 a | 105.6 abc | 144.6 ab | 128.5 a | 80.5 ab |
| laminate-1989 | 74.4 a | 114.1 ab | 157.2 a | 144.7 ab | 58.5 c |
| PVC/twine | 43.9 bc | 111.9 ab | 135.3 abc | 110.0 abc | 100.4 a |

[1]Within a column, means followed by the same letter are not significantly different at the 5% level of significance according to the Duncan's Multiple Range Test.

Based on the field test results, batch-to-batch variation in laminate dispensers is apparent since the 1988 laminate remained attractive longer than the 1989 laminate. This variation has been observed frequently in the past and, in part, motivated the search for an alternate dispenser. The PVC/twine dispenser gave higher moth captures than either laminate after 16 weeks of aging and, with the possible exception of the 0-time period, gave moth captures that were not significantly different from those with the better (1988) laminate. In addition, Test 2 included a cotton wick freshly treated with 100 mg of (+)-disparlure, the standard adopted by APHIS for assessing efficacy of all dispensers, and the results show that the moth capture of the PVC/twine dispenser at all aging periods was not significantly different from the standard.

TABLE 3

Mean numbers of males[1] captured per trap in each of four observations in Test 2, 7/23–7/27, 1989.

| Dispenser | Weeks of Greenhouse Aging | | | | |
|---|---|---|---|---|---|
| | 0 | 4 | 8 | 12 | 16 |
| laminate-1988 | 175.1 a | 159.6 abc | 124.0 a–d | 130.3 a–d | 97.5 cd |
| laminate-1989 | 161.0 ab | 145.1 abc | 102.4 b–d | 95.5 b–d | 58.7 e |
| PVC/twine Cotton 100 µg | 111.2 a–d 154.1 ab | 130.6 a–d | 124.7 a–d | 83.4 d | 135.1 a–d |

[1]Means throughout the table followed by the same letter are not significantly different at the 5% level of significance according to the Duncan's Multiple Range Test.

Example IV

Laboratory Test

A laboratory test was conducted to compare the release rates of the PVC/twine dispenser and the 1989 laminate dispenser as a function of duration of exposure in a laboratory oven at 59° C. under constant air flow of 100 ml/min. These conditions were used to accelerate the loss of pheromone. The release rates were measured periodically at 35° C., and the results are shown in FIG. 3. At the conclusion of the test (370 hr at 59° C.), the laminate dispensers contained an average of 0.09 mg and the PVC/twine dispensers an average of 118 mg of (+)-disparlure per dispenser. These data parallel those obtained on greenhouse-aged dispensers and again show that the PVC/twine dispenser slows the release of a nominal 500 mg dose of (+)-disparlure as compared to the conventional laminate dispenser. As a result, the duration of efficacy of the PVC/twine dispenser is longer than that of the laminate.

As shown by the Examples, a PVC-coated flexible dispenser has been invented which prolongs the duration of high attraction. Because of this dispenser's effectiveness, baited traps can be deployed in the field well in advance of insect flight. In addition, the dispenser can also replace both the twist tie and the laminate dispenser currently used to prepare traps.

It is understood that the foregoing detailed description is given merely by way of illustration and that modification and variations may be made therein without departing from the spirit and scope of the invention.

We claim:

1. A dispenser comprising a flexible support of multi-stranded material, having coated thereon a mixture of PVC and an insect attractant in an amount sufficient to lure an insect for which said attractant is effective.

2. The dispenser of claim 1, wherein the insect attractant is a pheromone.

3. An insect trap comprising a housing and the dispenser of claim 1 attached to the inside of said housing.

4. The dispenser of claim 1, wherein said flexible support is selected from the group consisting of twine, string, thread, and cord.

5. The insect trap of claim 3, wherein the insect attractant is a pheromone.

6. The insect trap of claim 5, wherein said trap additionally comprises an insecticide in an amount sufficient to kill an insect trapped within said housing.

7. A method of luring insects, wherein the trap of claim 3 is placed on a support in an area suspected of being infested with said insects, for a period of time sufficient to permit the attractant to effectively lure insects into the trap.

8. The method of claim 7, wherein the attractant is a pheromone.

9. The method of claim 8, wherein said trap additionally comprises an insecticide in an amount sufficient to kill an insect trapped within said housing.

10. The method of claim 9, wherein the period of time is one flight period.

\* \* \* \* \*